United States Patent [19]

Lesage et al.

[11] Patent Number: 4,961,916

[45] Date of Patent: Oct. 9, 1990

[54] SAMPLING DEVICE

[75] Inventors: Jacques Lesage, St. Hubert; Guy Perrault, Laval, both of Canada

[73] Assignee: IRSST-Institut de Recherche en Sante et en Securite du Travail du Quebec, Montreal, Canada

[21] Appl. No.: 201,176

[22] Filed: Jun. 2, 1988

[51] Int. Cl.[5] .......................... G01N 1/24; B01D 53/30
[52] U.S. Cl. ........................................ 422/88; 422/56; 422/57; 422/58; 422/101; 436/109; 55/270; 55/318; 55/387; 55/487; 73/863.21; 73/863.23
[58] Field of Search ...................... 422/56, 57, 58, 61, 422/83, 88, 101; 55/270, 316, 318, 387, 485, 487, DIG. 33; 73/863.21, 863.23; 210/497.01, 500.25, 500.26, 500.27, 500.29, 508, 510.1; 436/109, 128

[56] References Cited

U.S. PATENT DOCUMENTS

| 2,577,607 | 12/1951 | Conley | 128/142 |
|---|---|---|---|
| 4,141,703 | 2/1979 | Mulchi | 55/316 |
| 4,178,794 | 12/1979 | Jugle et al. | 73/28 |
| 4,187,390 | 2/1980 | Gore | 174/102 |
| 4,191,821 | 4/1980 | Gloriod | 528/501 |
| 4,263,144 | 4/1981 | Platt | 210/658 |
| 4,350,507 | 9/1982 | Greenough et al. | 55/270 |
| 4,380,587 | 4/1983 | Koochev | 436/128 |
| 4,455,881 | 6/1982 | Clark et al. | 73/863.21 |
| 4,570,494 | 2/1986 | Dunn et al. | 73/863.21 X |
| 4,613,575 | 9/1986 | Westrup et al. | 436/106 |
| 4,689,059 | 8/1987 | Magdelain | 55/382 |
| 4,692,175 | 9/1987 | Frantz | 55/218 |
| 4,721,517 | 1/1988 | Cloutier | 55/270 |
| 4,790,857 | 12/1988 | Miksch | 422/61 X |
| 4,858,476 | 8/1989 | Tobin | 73/863.23 |
| 4,902,318 | 2/1990 | Stevens et al. | 55/270 |

FOREIGN PATENT DOCUMENTS

| 0470814 | 11/1972 | Australia | 55/270 |
| 0279069 | 8/1988 | European Pat. Off. | 436/128 |

OTHER PUBLICATIONS

G. Skarping et al., J. of Chromatography, 346 (1985) pp. 191-204, Elsevier Science Publisher B. V., Amsterdam,.

Capillary Gas Chromography Method for the Determination of Complex Mixture of Isocyanates and Amines. S. P. Chattopadhyay et al., Current Science, Jul. 5, 1987, vol. 56, No. 13, pp. 646-648, A New Spectrophotometric Reagent for Determination of Sulfur-Dioxide and Formaldehyde.

R. W. Bishop et al., Am. Ind. Hyg. Assoc. J. 44(3): 151-155 (1983), A Gas Chromatographic Procedure for the Determination of Airborne MDI and IDI.

K. S. Booth et al., State-of-the-Art, Monitoring and Analysis for Airborne Isocyanates.

R. McMahon, Using Microprocessor-Based Technology to Enhance the Measurement and Documentation of TDI/MDI Exposures.

(List continued on next page.)

Primary Examiner—Robert J. Warden
Assistant Examiner—Rebekah A. Griffith
Attorney, Agent, or Firm—Bacon & Thomas

[57] ABSTRACT

The invention relates to an improved sampling device for selectively collecting gaseous and aerosol pollutants contained in polluted air, said device being of the type comprising a cartridge provided with an inlet, an outlet and filtering means, a vacuum pump and means for connecting said pump to the outlet of the cartridge to cause some pulluted air to be drawn through said filtering means, the improvement wherein said filtering means consists of three successive filters and wherein: the first filter is made with a material of such a porosity that it collects aersol pollutants but is permeable to gas; the second filter is positioned downstream of the first filter and consists of a porous substrate impregnated with an effective amount of a chemical compound that reacts with one or more specific harmful or toxic gaseous pollutants to produce therefrom derivatives, said second filter being of such a porosity as to be permeable to air but not to said derivatives; and the third filter is positioned downstream of the second filter and consists of a porous material that is permeable to air and rigid enough to prevent deformation of the first and second filters. The invention also relates to a method using the above mentioned device.

5 Claims, 1 Drawing Sheet

OTHER PUBLICATIONS

R. K. Beasley et al., Analytical Chemistry, vol. 56, No. 9, Aug. 1984, pp. 1604–1608, Determination of Polymethylene Polyphenylene Isocyanate in Air by Size Exclusion Chromatography.

R. F. Walker et al., J. of Chromatography, 301 (1984) pp. 485–491, Elsevier Science Publisher, B. V. Amsterdam, Separation of Isocyanate Prepolymer Components as Their Urea Derivatives by Reversed-Phase High Performance Liquid Chromatography.

D. A. Bagon et al., Am. Ind. Hyg. Assoc. J. 45(1): 39–43 (1984) Evaluation of Total Isocyanate-in-Air Method Using 1-(2-Methoxyphenyl) Piperazine and HPLC.

K. Anderson et al., Am. Ind. Hyg. Assoc. J. 44(11): 802–808(1983) A Comparative Study of Solvent and Solvent-Free Sampling Methods for Airborne 4,4'-Diphenylmethane Diisocyanate (MDI) Generated in Polyurethane Production.

K. Anderson et al., Scand. j. Work Environ Health 9 (1983) 497–503, Monitoring 1,6-Hexamethylene Diisocyanate in Air by Chemosorption Sampling.

R. J. Rando et al., Am. Ind. Hyg. Assoc. J. 45(3): 199–203 (1984) Isomeric Composition of Airborne TDI in the Polyurethane Foam Industry.

National Institute for Occupational safety and Health, NIOSH-Manual of Analytical Methods, Method P & CAM 347 vol. 7 Cincinnati MIOSH (1981)-Isocyanate Analysis.

J. Keller et al., Am. Chem. Soc. (1979), Sampling of Isocyanates in Air.

C. J. Warwick et al., Analyst, Jun. 1981, vol. 106, pp. 676–685, Application of Electrochemical Detection to the Measurement of Free Monomeric Aromatic and Aliphatic Isocyanates in Air by High-Performance Liquid Chromatography.

C. L. Geraci Jr. et al., American Industrial Hygiene Conference Philadelphia, Pennsylvania, May 22–27, 1983 Chemical Characterization of TDI and TDI Product Exposures During Urethane Foam Fabrication.

C. Sangoö et al., J. of Liquid Chromatography 3(7), 971–990 (1980), A New Reagent for determination of Isocyanates in Working Atmosphere by HPLC Using UV or Fluorescence Detection.

K. Anderson et al., Analysis of Gaseous Diisocyanates in Air Using Chemsorption Sampling.

E. H. Nieminen et al., J. of Liquid Chromatography 6(3), 453–469 (1983) Simultaneous Determination of Aromatic Isocyanates and Some Carcinogenic Amines in the Work Atmosphere by Reversed-Phase High-Performance Liquid Chromatography.

R. F. Walker et al., Am. Ind. Hyg. Assoc. J. 42(5) 1981 pp. 392–397, Chemical Interference Effects in the Measurement of Atmospheric Toluene Diisocyanate Concentrations When Sampling with an Impregnated Paper Tape.

S. P. Levine et al., Analytical Chemistry, vol. 51, n° Jul. 8, 1979, Determination of Aliphatic Isocyanates in Air by a Liquid Chromatographic-Fluorescence Technique.

R. F. Walker et al., Analyst. 104 (Oct. 1979) pp. 928–935, Spectrophotometric Determination of Aliphatic Isocyanates in the Occupational Atmosphere.

D. A. Bagon et al., J. of Chrom. 190, 1980–pp. 175–182, Determination of Airborne Free Monomeric and Aliphatic Isocyanates by High-Performance Liquid Chromatography.

National Institute for Occupational Safety and Health-NIOSH, Isocyanate Analysis-NIOSH Method 5505.

POLLUTED AIR

TO THE PUMP

SAMPLING DEVICE

BACKGROUND OF THE INVENTION

1. Field of the invention

The present invention relates to an improved sampling device allowing one to collect separately gas and aerosol pollutants contained in polluted air, and to a method of use of this device.

2. Brief description of the prior art

U.S. Pat. No. 4,689,059 describes a device for cleaning harzardous or toxic solid and liquid substances and for effectively retaining the macro- and micro-particles of the substance along with any vapor generated thereby. This device generally comprises a vacuum cleaner having a housing and an arrangement for drawing a fluid flow from an inlet to an outlet of the housing. A first filter is provided for separating and retaining both macro- and micro-particles of the substance entrained with the fluid flow. The first filter is arranged on a downstream side of the inlet of the housing and has a reservoir portion arranged below the inlet. Walls of the first filter permit outflow of substantially only vapors of the substance entrained in the fluid flow. A second filter for retaining the vapors is arranged fluidically between the first filter and the outlet. This second filter is advantageously a carbon filter. In a particularly preferred embodiment, the first filter includes a microporous filter membrane which is laminated to a fibrous support to provide a self-supporting unitary first filter for accomplishing the separation of the macro- and micro-particles of the substance. Advantageously, this first filter is made with polytetrafluoroethylene especially a polytetrafluoroethylene filter of the type described in U.S. Pat. No. 4,187,390.

Also, as evidenced by U.S. Pat. Nos. 4,178,794; 4,350,507 and 4,455,881, there presently exists various types of devices to be worn by workmen for measuring the quantity of airborne particles in a given area of work.

More particularly, U.S. Pat. No. 4,178,794 describes a device intended to be worn on a workmen's chest. This device comprises a cartridge provided with an inlet, an outlet and an air filter, the inlet of the cartridge being connected to a cyclone which separates respirable and non-respirable airborne particles, while the outlet of said cartridge is connected to a portable vacuum pump.

U.S. Pat. No. 4,350,507 describes a device intended to be suspended either in front of a worker by use of straps passing around his neck and waist, or as an integral part of a helmet worn by said workman. This device comprises a housing defining an air passageway, an electric fan mounted in the passageway, a main filter located across the passageway to collect respirable airborne particles and a prefilter located across the passageway upstream of the main filter, to collect non-respirable airborne particles.

U.S. Pat. No. 4,455,881 describes a device intended to be worn by a workman for sampling respirable aerosols contained in an ambient atmosphere. This device comprises a selector capillary tube open at one end thereof to the atmosphere, a sampling capillary tube in fluid communication with the other end of the selector tube, and aspiration means in fluid communication with the sampling tube.

U.S. Pat. No. 4,721,517 describes a sampling device for collecting at least part of the airborne particles in a workman's breathing zone, said device being of the type comprising a cartridge provided with an inlet, an outlet and an air filter (e.g. a membrane of polyvinylchloride (PVC) or a membrane of cellulose esters having a porosity of about 0.8 $\mu$m), a vacuum pump and a piece of flexible tubing of determined length connecting the vacuum pump to the outlet of the cartridge so that a portion of the airborne particles in said breathing zone is drawn through said filter and is collected thereon.

Until now, there have been no devices nor methods for the separate collection of gaseous and aerosol pollutants contained in polluted air in order to make possible, thereafter, the quantitative determination of the amount of gaseous and aerosol pollutants that were contained in said polluted air.

SUMMARY OF THE INVENTION

A first object of the invention is to provide a device which overcomes the aforesaid drawbacks. More particularly, the first object of the invention is to provide an improved device which allows one to collect separatly gas and aerosol pollutants (e.g. gaseous isocyanates and aerosol isocyanates) contained in a polluted atmosphere.

Another object of the invention is to provide such an improved device which is compact, sturdy, easy to handle and optionally useable for personal sampling (e.g. it does not need any liquid, corrosive solution or powder for the sampling step).

Another object of the invention is to provide such an improved device which, when subsequently associated with an appropriate analysis system, allows the user to measure the amount of gas and aerosol pollutants (such as gaseous isocyanates and aerosol isocyanates) in a polluted atmosphere.

Another object of the invention is to provide a method of use of the device according to the invention to selectively determined the amount of gas and aerosol pollutants in a polluted atmosphere.

According to the invention, said device is of the type comprising a cartridge provided with an inlet, an outlet and filtering means, a vacuum pump and means for connecting said pump to the outlet of the cartridge to cause some polluted air to be drawn through said filtering means. In accordance with the invention, this device is improved in that the filtering means consists of three successive filters for selectively collecting gaseous and aerosol pollutants contained in a polluted atmosphere.

The first filter is made with a material of such porosity that it collects aerosol pollutants but is permeable to gas. Advantageously, this first filter is made from a material selected from the group consisting of polytetrafluoroethylene (TEFLON, trade mark), polyvinylchloride (PVC), polyester and polycarbonate. Preferably, the first filter is made of polytetrafluoroethylene and has a porosity comprised between 0.5 and 5 $\mu$m.

The second filter is positioned downstream of the first filter and consists of a porous substrate impregnated with an effective amount of a chemical compound that reacts with one or more specific harmful or toxic gaseous pollutants to produce therefrom harmless derivatives, said second filter being of such a porosity as to be permeable to air but not to said harmless derivatives. Advantageously, the porous substrate of the second filter is selected from the group consisting of glass fiber, mixed cellulose esters, silver grids, polypropylene and polyurethane foam.

Advantageously, the chemical compound that impregnates the second filter is selected amongst those listed hereinafter:

| gaseous air pollutants to be collected | chemical compound used in the second filter |
|---|---|
| aliphatics and aromatics isocyanates | secondary amines (advantageously 2-methoxyphenylpiperazine, 9-(N-methylaminomethyl) anthracene and nitrobenzyl-N-propylamine) |
| aromatics isocyanates | diethyl amine |
| isocyanates | monohydroxylated and non volatiles alcohols |
| aldehydes | $\beta$-hydroxylated secondary amines (advantageously benzylethanolamine, pentafluorobenzylethanolamine and 3,5-dinitrobenzylethanolamine) |
| fluorides | NaOH |
| aromatic polycyclic hydrocarbides | polyurethane foam |
| $SO_2$ | $PbO_2$ |
| $SO_2$ + formaldehyde | auramine (4,4' bis dimethylamino-benzophenone imide) |
| epoxydes | HBr |

Advantageously, alilpathic and armoatic isocyanates are selected from the group consisting of toluene diisocyanate (TDI), methylene biphenyldiisocyante (MDI) (especially the 4,4' isomer), isophorone diisocyante (IPDI) and hexamethylene diisocyanate (HDI) (especially the 1.6 isomer).

Advantageously, the porous support is selected from the groups consisting of cellulose esters, silver grids, polypropylene and polyurethane foams, and has a porosity comprised between 0.45 and 0.8 $\mu$m.

Preferably, the second filter is made of fiber glass impregnated with 9-(N-methylamino methyl) anthracene and has a porosity of 0.8 $\mu$m.

The third filter is positioned downstream of the second filter and consists of a porous material that is permeable to gas and rigid enough to prevent deformation of the first and second filters. Advantageously, this third filter consists of a porous pad filter having a porosity greater than 1.2 $\mu$m, said pad filter being a porous material selected from the group consisting of porous plastics, celluloses and metal grids.

The thickness of aforesaid filters may vary within a wide range without affecting the invention. Advantageously, each of these filters has a thickness that is much less than the diameter of its surface and each is particularly similar to the filters commonly used with existing filtering cartridges.

According to a preferred embodiment, the invention relates to a sampling device for selectively collecting gaseous isocyanates and aerosol isocyanates that are contained in polluted air, said device being of the type comprising a cartridge provided with an inlet, an outlet and filtering means, a vacuum pump and means for collecting said pump to the outlet of the cartridge to cause some polluted air to be drawn through said filtering means, the improvement wherein said filtering means consists of three successive filters and wherein:

the first filter is made with polytetrafluoroethylene and has a porosity selected between 0.8 and 5.0 $\mu$m in order to collect aerosol isocyanates but to be permeable to gas, the second filter is positioned downstream of the first filter, has a porosity of about 0.8 $\mu$m and consists of a fiber glass filter impregnated with an effective amount of 9-(N-methylaminomethyl) anthracene that reacts with the gaseous isocyanates to produce therefrom urea derivatives that are caught in said second filter, the third filter is positioned downstream of the second filter and consists of a porous pad filter having a porosity greater than 1.2 $\mu$m and made with a porous material rigid enough to prevent any deformation of the first and second filters and selected from the group consisting of porous plastics, celluloses and metal grids.

The invention is also concerned with a method for selectively determining the amount of gaseous and aerosol pollutants that are contained in polluted air, wherein a portion of the air containing aforesaid pollutants is drawn through the successive combination of filters of the aforesaid improved device, for a determined period of time and at a determined flow rate; and then the first and second filters are removed from the cartridge and separately subjected to an appropriate quantitative chemical analysis which allows one to determine the isocyanate content of each filter.

Advantageously, the invention is concerned with a method for selectively determining the amount of gaseous and aerosol pollutants that are contained in polluted air, which comprises the following steps:

Providing an improved device of the type comprising a cartridge provided with an inlet, an outlet and filtering means, a vacuum pump and means for connecting said pump to the outlet of the cartridge to cause some polluted air to be drawn through three successive filters. The first filter is made with a material of such porosity that it collects aerosol pollutants but is permeable to gas. The second filter is positioned downstream of the first filter and consists of a porous substrate impregnated with an effective amount of a chemical compound that reacts with one or more specific harmful or toxic gaseous pollutants to produce therefrom derivatives that are caught in said second filter which is of such a porosity as to be permeable to air but not to said derivatives. The third filter is positioned downstream of the second filter and consists of a porous pad filter having a porosity greater than 1.2 $\mu$m and being made with a porous material which is rigid enough to prevent deformation of the first and second filters (under the vacuum force) and is selected from the group consisting of porous plastics, celluloses and metal grids.

Operating the vacuum pump so as to draw a portion of the air containing aforesaid pollutants through said filtering means for a determined period of time and at a determined flow rate.

Removing the first and second filters from the cartridge.

Subjecting the first filter to a reacting or derivatisation solution, dry evaporating the reacting or derivatisation solution and dissolving the evaporation residue in a desorption solution and then measuring the polluant content of this latter solution with a high pressure liquid chromatograph (HPLC) provided with an appropriate detector (particularly a U.V. detector).

Subjecting the second filter to a desorption solution and then measuring the pollutant content of this desorption solution with a high pressure liquid chromatograph provided with an appropriate detector (particularly an U.V. detector and a fluorescence detector in series).

Advantageously, the first filter of the device used in the aforesaid method is made from a material selected from the group consisting of polytetrafluoroethylene (TEFLON, trade mark), polyvinylchloride (PVC), polyester and polycarbonate. Preferably, this first filter is made of polytetrafluoroethylene and has a porosity comprised between 0.5 and 5 μm.

Advantageously, the second filter of the device used in the aforesaid method consists of a porous substrate selected from the group consisting of glass fiber, mixed cellulose ester, silver grids, polypropylene and polyurethane foams. Preferably, this second filter is impregnated with a chemical compound selected amongst those listed hereinafter.

| gaseous air pollutants to be collected | chemical compound used in the second filter |
|---|---|
| aliphatics and aromatics isocyanates | secondary amines (advantageously 2-methoxyphenylpiperazine, 9-(N-methylaminomethyl) anthracene and nitrobenzyl-N-propylamine) |
| aromatics isocyanates | diethyl amine |
| isocyanates | monohydroxylated and non volatiles alcohols |
| aldehydes | β-hydroxylated secondary amines (advantageously benzylethanolamine, pentafluorobenzylethanolamine and 3,5-dinitrobenzylethanolamine) |
| fluorides | NaOH |
| aromatic polycyclic hydrocarbides | polyurethane foam |
| $SO_2$ | $PbO_2$ |
| $SO_2$ + formaldehyde | auramine (4,4' bis dimethylaminobenzophenone imide) |
| epoxydes | HBr |

Advantageously, aliphatic and aromatic isocyanates are selected from the group consisting of toluene dissocyanate (TDI), methylene biphenyldiisocyanate (MDI) (especially the 4,4' isomer), isophorone diisocyanate (IPDI) and hexamethylene diisocyanate (HDI) (especially the 1,6 isomer).

More particularly, the aforesaid porous support is selected from the groups consisting of cellulose esters, silver grids and polypropylene and has a porosity comprised between 0.45 and 0.8 μm and polyurethane foams of suitable density.

Preferably, the aforesaid second filter is made of glass fiber impregnated with 9-(N-methylaminomethyl) anthracene and has a porosity of 0.8 μm.

Advantageously, the third filter of the device used in the aforesaid method consists of a porous pad filter having a porosity greater than 1.2 μm, said pad filter being a porous material selected from the group consisting of porous plastics, celluloses and metal grids.

The thickness of aforesaid filters may vary within a wide range without affecting the invention. Advantageously, each of these filters has a thickness that is much less than the diameter of its surface and each is similar to the filters commonly used with existing filtering cartridges.

More particularly, the invention is concerned with a method for selectively determining the amount of gaseous and aerosol isocyanates that are contained in polluted air, which comprises the following steps:

providing an improved device of the type comprising a cartridge provided with an inlet, an outlet and filtering means, a vacuum pump and means for connecting said pump to the outlet of the cartridge to cause some polluted air to be drawn through three successive filters, the first filter being made with polytetrafluoroethylene and having a porosity selected between 0.8 and 5.0 μm in order to collect aerosol isocyanates but to be permeable to gas, the second filter being positioned downstream of the first filter, having a porosity of about 0.8 μm and consisting of a glass fiber filter impregnated with an effective amount of 9-(N-methylaminomethyl) anthracene that reacts with gaseous isocyanates to produce therefrom urea derivatives that are caught in said second filter, and the third filter being positioned downstream of the second filter and consisting of a porous pad filter having a porosity greater than 1.2 μm and made with a porous material rigid enough to prevent any deformation of the first and second filters and selected from the group consisting of porous plastic, cellulose and metal grids;

operating the vacuum pump so as to draw a portion of the air containing aforesaid isocyanates through said filtering means for a determined period of time and at a determined flow rate;

removing the first and second filters from the cartridge;

subjecting the first filter to a reacting or derivatisation solution, dry evaporating the reacting or derivatisation solution and dissolving the evaporation residue in a desorption solution, and then measuring the isocyanate content of this latter solution with a high pressure liquid chromatograph provided with a UV detector; and subjecting the second filter to a desorption solution and then measuring the contents of the solution in isocyanates with a high pressure liquid chromatograph provided with a UV detector and a fluorescence detector, in series.

Advantageously, each filter is a disc of about 37 mm diameter, the period of time is comprised between 2 minutes and 4 hours (preferably about 15 minutes) and the determined flow rate is comprised between 0.5 and 2.0 L/min (preferably 1 L/min).

Advantageously, the isocyanate content of the first or second filter is refered to an appropriate calibration curve so as to determine the concentration of gaseous or aerosol isocyanates in the polluted air.

BRIEF DESCRIPTION OF THE DRAWINGS

The invention will be better understood with reference to the following non-restrictive description of preferred embodiments thereof, taken in connection with the accompanying drawings in which.

DESCRIPTION OF PREFERRED EMBODIMENTS

Figure 1:
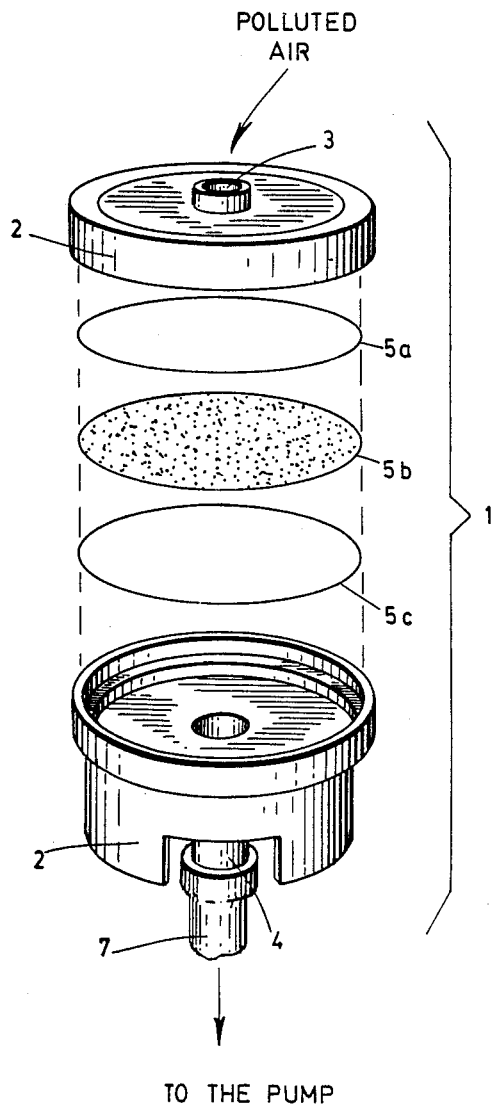
FIG. 1 is an exploded perspective view of a cartridge according to the invention.
Figure 2:
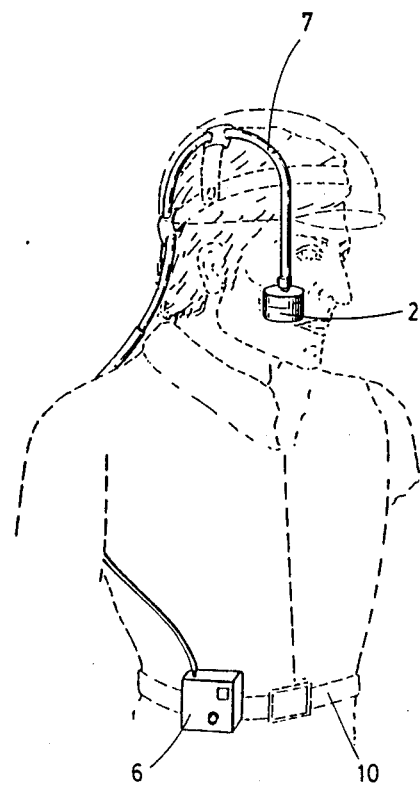
FIG. 2 is a perspective view of the device of FIG. 1 worn by a workman.

The improved device 1 according to the invention as shown in FIG. 1 of the accompanying drawings, comprises a cartridge 2 (especially a cylindrical plastic cartridge having 25 mm inside diameter or preferably 37 mm inside diameter) provided an inlet 3 defining an air intake (which may be optionally worn by a workman and preferably positioned within the breathing zone of this workman (see FIG. 2)), a tubular outlet 4 and three successive filters 5a, 5b and 5c stacked one above the other and positioned inside the cartridge between the inlet 3 and the outlet 4 so that a stream of polluted air (see arrow) passes through said filters to a vacuum pump (not shown in FIG. 1) via a piece of flexible tubing 7 (partly shown).

The filter 5a consists of a membrane of polytetrafluoroethylene (TEFLON) having a preferred porosity of about 0.8, 1.0 or 5.0 $\mu$m so as to collect aerosol isocyanates while being permeable to gaseous isocyanates.

The filter 5b consists of a membrane of glass fibers having a porosity of about 0.8 $\mu$m impregnated with an efficient amount of 9-(N-methylamino methyl) anthracene (MAMA). The 9-(N-methylamino methyl) anthracene reacts with the gaseous isocyanates that enter the filter 5b to produce therefrom urea derivatives that are caught in said filter 5b.

The filter 5c consists of a membrane of porous plastics having a porosity greater than 1.2 $\mu$m. This membrane is rigid enough to prevent deformation of filters 5a and 5b under the vacuum force applied by the pump. Also, this membrane promotes a uniform flow of air through the filters but does not collect chemical compound which is caught by the second filter 5b.

The cartridge 2 is advantageously provided with means for supporting the filters and is made of two parts engageable one into the other to allow an easy positioning of the filters 5a, 5b and 5c and to allow recover of filters 5a and 5b for analysis purposes.

Advantageously, one part of the cartridge 2 is provided with a circular edge and an outer cylindrical surface, and the other part is provided with a circular shoulder and an inner cylindrical surface. Eventually, both aforesaid surfaces are threaded. When said parts are engaged one into the other or screwed together by engagement of their corresponding threaded cylindrical surfaces, the filters 5a, 5b and 5c are pinched between said edge and shoulder. A cellulose adhesive tape may be applied to seal both parts of the cartridge.

The flexible tubing 7 may be made of TYGON (trade mark) and have one end thereof forced over the free end of the outlet 4 in order to define an airtight connection, while the opposite end of this tubing is forced over a cylindrical tubular inlet of the pump.

The pump is advantageously of the type provided with rechargeable cells and has to be operable for the entire period of sampling (e.g. up to 4 hours). This pump, when intended for personal sampling, must be as light as possible so that it does interfere with the work of the workman while it provides a steady and regular stream of air (without pulses) at a low flow rate (e.g. 0.5 to 2 L/min) through the filters during the entire period of sampling.

To use a device as shown in FIG. 1, a workman (see FIG. 2) has to carry out the following steps:

(i) Disengage both parts of the cartridge 2, one of said parts being provided with a circular edge and an optionally threaded, outer cylindrical surface, and the outer part being provided with a circular shoulder and an optionally threaded, inner cylindrical surface, said surfaces or threaded surfaces being complimentary(i.e. intended to fit one into the other).

(ii) Position between the edge and shoulder, the filters 5a, 5b and 5c of appropriate size, said filters being stacked one above the other, (filter 5a must be positionned near the air intake of the cartridge), and then reengage or rescrew said parts of the cartridge 2 till the edge and shoulder pinch the filters 5a, 5b and 5c.

(iii) Pass the flexible tubing 7 through openings of strips.

(iv) Force the end of the tubing 7 over the cylindrical outlet 4 of the cartridge 2, the other end of the tubing 7 being forced over the cylindrical inlet of a portable vacuum pump 6.

(v) Fasten the tubing 7 in a conventional manner to position the cartridge 2 in the breathing zone and then fix the pump 6 to his belt 10 in a conventional manner. Advantageously, the pump 6 is fixed to the workman's belt with a clip forming an integral part of said pump.

(vi) Position in a conventional manner the cartridge 2 in breathing zone.

(vii) Switch on the pump 6 at a determined flow rate for a determined period of time, and do his professional work.

(viii) Stop the pump 6 and give the cartridge 2 to a technician for analysis purposes.

Alternatively, the aforesaid device can be put in any conventional manner at a determined location in an area of work without having to be worn by a workman. Then, aforesaid steps (iii), (v) and (vi) are simply omitted.

More particularly, for selectively determining the amount of gaseous and aerosol isocyanates (especially gaseous and aerosol hexamethylene diisocyanates (HDI) in example 1 and 2 reported hereinafter) that are contained in polluted air, with a device as shown in FIG. 1, the following procedure is followed.

A cartridge 2 is equipped with filters 5a, 5b and 5c as pointed out in step (ii) above. Preferably, the polytetrafluoroethylene filter 5a is positioned first, then the fiber glass membrane 5b impregnated with 9-(N-methylaminomethyl) anthracene and then the porous plastic membrane 5c.

During the sampling, which is carried out as pointed out in step (vii) above, 15 liters of polluted air (especially containing gaseous and aerosol HDI) are drawn through the cartridge 2 at a flow rate of 1 liter/minute for 15 minutes. Said cartridge 2 has a filter 5a made of polytetrafluoroethylene (TEFLON, trade mark) having a porosity of about 0.8 $\mu$m, a filter 5b made of glass fiber having a porosity of 0.8 $\mu$m and impregnated with 9-(N-methylaminomethyl) anthracene, and a filter 5c made of porous plastic and having a porosity greater than 1.2 $\mu$m.

Immediately after the sampling (i.e. after step (viii) above) the filter 5a is recovered from the cartridge 2 with tongs, dipped in a flask containing 5.0 mL of an absorption solution and shaken well. (The absorption solution is obtained by weighing 100 mg of 1-(2-methoxyphenyl)-piperazine (MOPIP) and diluting it in 100 mL of toluene to give a stock solution, and then diluting 10 mL of this stocksolution in 100 mL of toluene). Then the solution contained in the flask is transferred to a test tube and washed three times with toluene.

The solution contained in the test tube is dry evaporated and then 1.0 mL of a desorption solution is added. (This desorption solution is obtained by diluting 500 $\mu$L of acetic anhydride to 100 mL with acetonitrile). The resulting solution is transferred with a Pasteur pipette into a flask, and then injected into a high pressure liquid chromatograph HPLC) coupled to a UV detector. (column: $C_{18}$ ODS-1, 5 $\mu$m (15 cm), mobile phase: 62% acetonitrile/38% buffer).

The aforesaid buffer is prepared by dissolution of 12.5 g of sodium acetate in one liter of water, acidification of the resulting solution to pH=6 with glacial aceticacid-(using a pH-meter) and then filtration of said solution under vacuum on a 0.45 μm filter. Helium is used to degasify the mobile phase).

According to methods well known to chemists, a calibration curve can be established to determine the concentration of aerosol HDI in the polluted air sampled. With the method according to the invention, a calibration curve is linear from 1.90 to 18.9 μg of HDI/m L of desorption solution. This corresponds to 0.13 to 1.26 mg of HDI/m$^3$ of a sample volume of polluted air (15 liters). The sensitivity of the method allows one to measure a minimal concentration of 0.12 μg of monomeric HDI/mL of desorption solution.

After the sampling (i.e. after step (viii) mentioned above), the filter 5b is recovered from the cartridge 2 with tongs, dipped in a flask containing 2.0 ml of a desorption solution (in order to desorbe the urea derivative from the filter 5b), shaken well for 30 minutes and the resulting solution is then injected into a high pressure liquid chromatograph.

The desorption solution is obtained by measuring out into a graduated cylinder 66 mL of dimethylformamide and adding to it 33 mL of a mixture consisting of 70% acetonitrile/30% buffer. (The buffer is obtained by adding 30 ml of triethylamine in one liter of water, acidifying the resulting mixture to pH=3.0 with phosphoric acid (using a pH-meter) and then filtering the resulting mixture under vacuum on a 0.45 μm filter).

The chromatographic conditions are the following:

| Column | $C_{18}$ ODS-1, 5 μm (15 cm) | |
|---|---|---|
| Mobile phase | 70% acetonitrile/30% buffer (degasified with He) | |
| Flow rate of the mobile phase | 2 mL/min | |
| UV detector | λ 254 nm | |
| Fluorescence detector | λ (emission) | 412 nm |
| | λ (excitation) | 254 nm |
| | slit | 10 |
| | mode | Energy |

According to methods well known to chemists, a calibration curve can be established to determine the concentration of gaseous HDI in the polluted air sampled. With the method according to the invention, a calibration curve is linear from 0.02 to 4.2 μg of HDI/2 mL of desorption solution. This corresponds to concentration of 0.001 to 0.28 mg of HDI/m$^3$ of a sampled volume of polluted air (15 liters). The sensitivity of the method allows one to measure 0.02 μg of HDI/1 m$^L$ of desorption solution (0.001 mg of HDI/m$^3$ of sampled air (15 liters)) and to detect 0.0005 mg of HDI/m$^3$ of sampled air (15 liters)).

To prepare a glass fiber filter impregnated with MAMA (9-(N-methylaminomethyl) antracene), said glass fiber filter is calcinated in an oven at 400° C. for 4 hours to eliminate any organic substances. The filters are soaked in an impregnation solution for 30 minutes and dried in a hood in the absence of light. (The impregnation solution is obtained by weighing 220 mg of MAMA and disolving it in 1.0 liter of toluene).

EXAMPLE 1

Sampling conditions

Sampling was carried out in a painting room of 3 276 ft$^3$ (14 ft×26 ft×9 ft) having a cross draft ventilation system, using a device as shown in FIG. 1. The results of this sampling were obtained with the aforesaid methods of analysis for filters 5a and 5b.

Isocyanate sampling was carried out during the application of a paint of trade mark DUPONT and the isocyanate involved was the hexamethylene diisocyanate (HDI) present in the hardener DUPONT 793-S. The painter applied a three coats of paint and three sets of samples were taken: the first during the application of the first layer of paint, the second set during the application of the second and third layers of paint, and the third set 18 minutes after the last application of paint.

For each set of samples, five extracts were taken four at fixed stations(A, B, C, D) and a fifth within the breathing zone of the painter. The four fixed stations were distributed at different locations in the painting room and at different heights. These extracts at fixed stations were intended to determine the distribution of isocyanates in the painting room.

The extract within the breathing zone of the painter was made with a pump worn by him during his work. This kind of extract was intended to evaluate the exposure of the painter to isocyanates during the application of paints (or lacquers).

Results

Table 1 shows the isocyanate concentration measured during paint application and table 2 shows isocyanate concentration measured 18 minutes after the last application. It should be noted that the analysis results shown hereinafter are directed to the HDI in various forms.

The terms aerosol (fine drops) and gas refer to physical aspects of HDI. The terms monomer and oligomer refer to chemical aspects of HDI. The monomer is the simplest form of HDI and the oligomer is a chemical compound consisting of a few monomers bound together with other products.

TABLE 1:

| Concentration in isocyantes during painting (mg/m$^3$) | | | | | |
|---|---|---|---|---|---|
| | Ambient air | | | | Breathing zone |
| | A | B | C | D | of the painter |
| HDI, monomer, gaseous | | | | | |
| 1st application | 0.108 | 0.058 | 0.064 | 0.101 | 0.025 |
| 2nd and 3rd applications | 0.089 | 0.035 | 0.052 | 0.089 | 0.021 |
| HDI, monomer, aerosol | | | | | |
| 1st application | 0.057 | 0.019 | 0.031 | 0.043 | ND |
| 2nd and 3rd applications | 0.033 | 0.019 | 0.024 | 0.046 | ND |
| HDI, monomer, total (aerosol + gas) | | | | | |
| 1st application | 0.165 | 0.077 | 0.095 | 0.144 | 0.025 |
| 2nd and 3rd applications | 0.122 | 0.054 | 0.076 | 0.135 | 0.021 |
| HDI, oligomer, aerosol | | | | | |
| 1st application | 3.14 | 1.14 | 1.50 | 2.08 | 0.55 |
| 2nd and 3rd applications | 3.00 | 0.77 | 1.12 | 1.89 | 0.38 |

ND = non detected:
<0.01 mg/m$^3$ (monomer, gas)
0.008 mg/m$^3$ (aerosol)

TABLE 2:

| Concentration in isocyanated 18 minutes after the last application of the paint (mg/m$^3$) | | | | |
|---|---|---|---|---|
| | Ambient air | | | |
| | A | B | C | D |
| HDI, monomer, gaseous | 0.001 | ND | 0.001 | 0.001 |
| HDI, monomer, aerosol | ND | ND | ND | ND |

TABLE 2:-continued

| Concentration in isocyanated 18 minutes after the last application of the paint (mg/m³) | | | | |
|---|---|---|---|---|
| | Ambient air | | | |
| | A | B | C | D |
| HDI, oligomer, aerosol | ND | ND | ND | ND |

ND = non detected:
<0.008 mg/m³ (aerosol)
<0.001 mg/m³ (gas)

Remarks

Changes int eh type of paint used or in ambient conditions (temperature, humidity) and in ventilation parameters would affect the results.

During the application of the paint, isocyanates were mainly in the form of aerosols (e.g. in the form of fine liquid drops suspended in air). A low proportion of isocyanates was present in the gaseous state.

Isocyanate concentration (gaseous and aerosol) is lower during the second and third paint applications. This may be explained by the reduced amount of paint used and, possibly, by the fact that isocyanates are evacuated by the ventilation before the third application.

Isocyanate concentration is higher when the extracting stations are close to the ground (A, D, C, B). This corroborates the fact that aerosol isocyanates are the heavier and fall faster to the ground. Furthermore, stations A and D are located near the extraction grids and are thus in the air flow.

The concentration of monomeric isocyanates (total) in the ambient air varies from 0.054 to 0.165 mg/m³, while in the breathing zone of the painter, the concentration is about 0.025 mg/m³.

The concentration of oligomeric isocyanates varies from 0.77 to 3.14 mg/m³ of ambient air and within the breathing zone of the painter the concentration is about 0.55 mg/m³.

18 minutes after the last application of paint, a 15-minute sampling according to the invention, shows that only traces of gaseous monomeric isocyanates of about 0.001 mg/m³ were present.

EXAMPLE 2

Sampling conditions

The sampling was carried out in a painting room of 2688 ft³ (14 ft×25 ft×8 ft) having a down draft ventilation system.

The sampling of isocyanates was carried out during the application of a lacquer (clear coat) sold under the trade mark SIKKENS and the isocyanate involved was the hexamethylene diisocyanate (HDI) present in the hardener SIKKEN MS. The painter applied two coats of lacquer and three sets of samples were taken: the first and second sets during the application of the first and second layers of lacquer respectively and the third, 25 minutes after the second application of lacquer.

For each set of samples, five extracts were taken: four at fixed stations (A, B, C, B) and a fifth within the breathing zone of the painter. The four fixed stations were distributed at different locations and at different heights. These extracts at fixed stations were intended to determine the distribution of isocyanates in the painting room.

The sample drawn in the breathing zone of the painter was made with a pump worn by him during his work. This kind of extract was intended to evaluate the exposure of the painter to isocyanates during the application of paints or lacquers.

Results

Table 3 shows the isocyanate concentration measured during both applications of lacquer, and table 4 shows the concentration measured 25 minutes after the second application. It should be noted that the analysis results shown hereinafter are directed HDI in various forms.

The terms aerosol (fine drops) and gas refer to physical aspects of HDI. The terms monomer and oligomer refer to chemical aspects of HDI. The monomer is the simplest form of HDI and the oligomer is a chemical compound consisting of a few monomers bound together with other products.

TABLE 3:

| Concentration in isocyanates during the application of the laquer (mg/m³) | | | | | |
|---|---|---|---|---|---|
| | Ambient air | | | | Breathing zone |
| | A | B | C | D | Personal |
| HDI, monomer, gaseous | | | | | |
| 1st application | 0.013 | 0.005 | 0.005 | 0.011 | 0.006 |
| 2nd application | 0.015 | 0.004 | 0.006 | 0.013 | 0.007 |
| HDI, monomer, aerosol | | | | | |
| 1st application | ND | ND | ND | ND | ND |
| 2nd application | ND | ND | ND | ND | ND |
| HDI, oligomer, aerosol | | | | | |
| 1st application | 2.53 | 0.91 | 0.72 | 2.15 | 0.94 |
| 2nd application | 3.75 | 0.54 | 1.21 | 2.85 | 1.36 |

ND = non detected:
<0.001 mg/m³ (gas monomer)
<0.008 mg/m³ (aerosol)

TABLE 4:

| Concentration in isocyanates 25 minutes after the application (mg/m³) | | | | |
|---|---|---|---|---|
| | Ambient air | | | |
| | A | B | C | D |
| HDI, monomer, gaseous | ND | ND | ND | ND |
| HDI, monomer, aerosol | ND | ND | ND | ND |
| HDI, oligomer, aerosol | ND | ND | ND | ND |

ND = non detected: <0.0001 mg/m³ gas monomer)
<0.0008 mg/m³ (aerosol)

Remarks

Changes in the type of lacquer used, in ambient conditions (temperature, humidity) and in ventilation parameters would affect the results.

During the application of the lacquer, isocyanates were mainly in the form of aerosols (i.e. in the form of fine liquid drops suspended in the air). A low proportion of isocyanates was present in a gaseous state.

Except at one station, the isocyanate concentration increased during the second application. It being known that the amount of lacquer used is lower during the second application, it may be supposed that isocyanates emitted during the first application were not completely evacuated by the ventilation system. It is also possible that the lacquer adherence be less during the second application thus increasing the proportion of isocyanate in the air.

Only station b does not follow the aforesaid rule and shows a lower concentration at the second application. This may be explained by the fact that station B is located at a height of 55 inches (i.e., higher than the application zone in this particular case).

The concentrations measured at stations A and D are higher than those measured at stations B and C. This can be explained by the fact that the air speeds measured in the zone of stations B and C (between 0.4 and 0.6 m/s) were greater than those measured in the zone of stations A and D (lower than 0.1 m/s). Furthermore, station A is located about 5 inches above the ground and is thus more likely to collect falling particles. Station D is located 32 inches above the ground and is thus lower than stations B and C.

The concentration int he ambient air varies from 0.004 mg/m$^3$ to 0.0015 mg/m$^3$ in monomeric isoyanate and the concentration in the breathing zone of the painter was of about 0.007 mg/m$^3$.

The concentration in oligomeric isocyanates in the ambient air varies from 0.72 to 3.75 mg/m$^3$, and the concentration in the breathing zone of the painter is of about 1.36 mg/m$^3$.

25 minutes after the last application (Table 4), the isocyanates were completely evacuated from the painting room.

What is claimed is:

1. In a sampling device for selectively collecting gaseous isocyanates and aerosol isocyanates that are contained in polluted air, said device being of the type comprising a cartridge provided with an inlet, an outlet and filtering means, a vacuum pump and means for connecting said pump to the outlet of the cartridge to cause some polluted air to be drawn through said filtering means, the improvement wherein said filtering means consists of there successive filters and wherein:

the first filter is made with polytetrafluoroethylene of such a porosity that it collects aerosol pollutants but is permeable to gas, the second filter is positioned downstream of the first filter and consists of a porous substrate impregnated with an effective amount of a secondary amine that reacts with the gaseous isocyanates to produce therewith urea derivatives, said second filter being of such a porosity as to be permeable to air but not to said derivative; and the third filter is positioned downstream of the second filter and consists of a porous material that is permeable to gas and rigid enough to prevent deformation of the first and second filters.

2. The improved device of claim 1, wherein the gaseous isocyanates to be collected are aliphatic and aromatic isocyanates and the secondary amine used in the second filter is selected from the group consisting of 2-methoxyphenylpiperazine, 9-(N-methylaminomethyl) anthracene and nitrobenzyl-N-propylamine.

3. The improved device of claim 1, wherein the porous substrate of the second filter is selected from the group consisting of mixed cellulose esters, silver grids and polypropylene and has a porosity comprised between 0.45 and 0.8 μm, and polyurethane foams of suitable density.

4. The improved device of claim 1, wherein the second filter is made of glass fiber impregnated with 9-(N-methylaminomethyl) anthracene and has a porosity of 0.8 μm.

5. In a sampling device for selectively collecting gaseous isocyanates and aerosol isocyanates that are contained in polluted air, said device being of the type comprising a cartridge provided with an inlet, an outlet and filtering means, a vacuum pump and means for connecting said pump to the outlet of the cartridge to cause some polluted air to be drawn through said filtering means, the improvement wherein said filtering means consists of three successive filters and wherein:

the first filter is made with polytetrafluoroethylene having a porosity selected between 0.8 and 5.0 μm in order to collect aerosol isocyanates but to be permeable to the gas, the second filter is positioned downstream of the first filter, has a porosity of about 0.8 μm and consists of a glass fiber filter impregnated with an effective amount of 9-(N-methylaminomethyl) anthracene that reacts with the gaseous isocyanates to produce therewith urea derivatives that are caught in said second filter, the third filter is positioned downstream of the second filter and consists of a porous pad filter porosity greater than 1.2 μm and made with a porous material rigid enough to prevent any deformation of the first and second filters and selected in the group consisting of porous plastics, celluloses and metal grids.

* * * * *